United States Patent
Daikeler et al.

(10) Patent No.: US 8,257,694 B2
(45) Date of Patent: Sep. 4, 2012

(54) NUTRITIONAL COMPOSITIONS FOR REDUCING OXIDATIVE DAMAGE

(75) Inventors: Carl D. Daikeler, Malibu, CA (US); Isabelle B. Daikeler, Malibu, CA (US); Darin L. Olien, Malibu, CA (US)

(73) Assignee: Product Partners, LLC, Santa Monica, CA (US)

( * ) Notice: Subject to any disclaimer, the term of this patent is extended or adjusted under 35 U.S.C. 154(b) by 384 days.

(21) Appl. No.: 12/466,158

(22) Filed: May 14, 2009

(65) Prior Publication Data

US 2010/0291050 A1    Nov. 18, 2010

(51) Int. Cl.
*A01N 63/00* (2006.01)
(52) U.S. Cl. .................. 424/93.44; 424/93.45; 424/94.1; 424/94.2; 424/195.15; 424/195.16; 424/195.17; 424/725; 424/729; 424/732; 424/736; 424/750; 424/752; 424/765; 424/766; 424/777
(58) Field of Classification Search ........................ None
See application file for complete search history.

(56) References Cited

OTHER PUBLICATIONS

Carl Daikeler "Carl Daikeler's Blog, Play, Shake, and Share", Jun. 16, 2008, 2 pages of PDF.*
International Search Report and Written Opinion of corresponding International Application No. PCT/US2010/034986 dated Jul. 29, 2010; total 13 pages.
Harden, "Shakeology, The Healthiest Meal of the Day", http://www.extremely-fit.com/fitness-tips/2009/03/shakeology-healthiest-meal-day, Mar. 24, 2009, XP002591287.
Anonymous: "Shakeology Meal Replacement Shake is the Healthiest Meal of the Day", http://www.extremely-fit.com/shakeology-meal-replacement-shake.html, Mar. 29, 2009, XP002591288.
Anonymous: "Shakeology—The Healthiest Meal of the Day—Greenberry", http://www.extremely-fit.com/downloads/ShakeologyGreenBerry.pdf,Dec. 31, 2008, XP002591289.
Adams, "Product review: LivingFuel Rx Super Greens superfood powder delivers a powerhouse of nutrition with no junk fillers", http://www.naturalnews.com/021637.html, Feb. 22, 2007, XP002591290.
Anonymous: "Livingfuel Supergreens—Optimized Whole Meal Superfood for Maximum Daily Nutrition", http://www.livingfuel.com/product_labels/NewSuperGreens.pdf, Feb. 22, 2007, XP002591291.

* cited by examiner

*Primary Examiner* — Kade Ariani
(74) *Attorney, Agent, or Firm* — Connolly Bove Lodge & Hutz LLP

(57) ABSTRACT

A nutritional composition for reducing oxidative damage and lipid peroxidation in humans, while allowing for the oxidative reactions necessary to sustain vital biological functions. The nutritional compositions comprise adaptogens comprising astragalus root, ashwagandha root, cordyceps, holy basil leaf, maca root, reishi mushrooms, schisandra, and suma root; superfoods comprising acerola, camu-camu, pomegranate, bilberry, blueberry, Goji berries, Acai, maitake, citrus bioflavonoids, rose hips, and Gingko biloba; probiotics comprising *Bifidobacterium longum, Lactobacillus acidophilus, Lactobacillus acidophilus* DDS-1, *Lactobacillus bulgaricus, Lactobacillus casei*, and *Streptococcus thermophilus*; and enzymes comprising amylase, papain, cellulase, lactase, lipase, protease, and bromelain. The nutritional compositions may also be provided as a meal replacement and further comprise one or more plant products, algae, vitamins, minerals, protein and methylsulfonylmethane (MSM).

15 Claims, No Drawings

NUTRITIONAL COMPOSITIONS FOR REDUCING OXIDATIVE DAMAGE

FIELD OF THE INVENTION

The present disclosure relates to a nutritional composition and, more particularly, to a nutritional composition for reducing oxidative damage in humans.

BACKGROUND

The scientific literature is replete with studies confirming the role of proper diet and nutrition in overall health and in preventing a variety of diseases. For example, a diet rich in fruits and vegetables has been long believed to help protect against a myriad of chronic diseases, such as cardiovascular disease and certain cancers.

Despite the importance of proper diet and nutrition, it remains a persistent and daily challenge for most people to prepare meals that meet all of the body's nutritional requirements. This is especially true for those who have busy and fast-paced lifestyles. Unfortunately, many resort to fast food, as they are daunted by the challenges of both knowing what their nutritional needs are and finding the appropriate food combinations to meet those needs. Malnutrition and obesity are among the many undesirable consequences of a fast/junk food diet.

More recently, antioxidants have received considerable attention and the role of antioxidants on health and disease prevention has been the subject of research. Antioxidants are believed to provide a variety of health benefits by reducing oxidative reactions and free radical formation in the body. Oxidative reactions have been linked to a number of disease states. It is a common misconception, however, that all oxidative reactions in the body are harmful.

Certain oxidative reactions, such as reduction-oxidation ("redox") reactions and signaling, are critical for sustaining life. Biological energy is frequently stored and released by means of redox reactions. Cellular respiration, for example, involves the oxidation of glucose to carbon dioxide and the reduction of oxygen to water. The process of cell respiration also depends heavily on the oxidation of NADH to NAD+. Thus, a paradox in metabolism is that while the vast majority of complex life on Earth requires oxygen for its existence, oxygen is a highly reactive molecule that is capable of damaging living organisms by producing reactive oxygen species.

Thus, an effective antioxidant system does not remove oxidants entirely, but instead keeps them at an optimum level. The relative importance and interactions between different antioxidants and between antioxidants and other compounds are very complex. The action of one antioxidant may depend on the proper function of other antioxidants, enzymes, and/or compounds. Also, the amount of protection provided by any one antioxidant will also depend on its concentration, its reactivity towards the particular reactive oxygen species being considered, and the status of the antioxidants with which it interacts. Moreover, consumption of excessive amounts of certain antioxidants has been found to be harmful to the body.

Thus, it is the complex mixture of antioxidants and other substances that provides the beneficial effects on the body. This is confirmed by studies showing the use of antioxidant vitamins alone as having no reduction in either the risk of developing heart disease or the rate of progression of existing disease. Indeed, a healthy body, through a proper nutrition, is usually able to maintain a complex network of antioxidants, enzymes and other compounds and biological components that work together to prevent damaging oxidative reactions, while at the same time allowing for the oxidative reactions which are necessary to sustain life. The proper nutrition required to sustain such a complex network, however, requires knowledge as to the body's precise nutritional requirements and the amount and combination of foods capable of fulfilling those requirements.

What is needed, therefore, is a composition which is capable of providing the nutrients needed to provide and support an effective antioxidant system in the body.

SUMMARY

The nutritional compositions disclosed herein have been shown to reduce oxidative damage in humans by providing the optimal combination and diversity of antioxidants, enzymes, probiotics, vitamins and minerals, while allowing for the oxidative reactions necessary to sustain vital biological functions.

The results of independent clinical trial, in which the nutritional composition was administered to human subjects over a period of thirty (30) days, evidences the synergistic effect resulting from the combination of the ingredients provided in the nutritional compositions disclosed herein. An average reduction of 39% of oxidative damage and lipid peroxidation was observed in the subjects, with the greatest reduction in one subject of up to 90%.

In accordance with a preferred embodiment, the nutritional composition comprises at least one adaptogen, at least one superfoods, at least one probiotic, and at least one enzyme. It is the combination of the adaptogens, superfoods, probiotics and enzymes which is believed to provide the synergistic effect of reducing oxidative damage in subjects.

The adaptogens may be any one or more selected from the group consisting of astragalus root, ashwagandha root, cordyceps, holy basil leaf, maca powder, reishi mushroom, schisandra powder, and suma powder.

The superfoods may be any one or more selected from the group consisting of: acerola, camu-camu, pomegranate, bilberry, blueberry, Goji berries, Acai, maitake, citrus bioflavonoids, rose hips, and *Gingko biloba*.

The probiotic may be any one or more selected from the groups consisting of: *Bifidobacterium longum, Lactobacillus acidophilus, Lactobacillus acidophilus*DDS-1, *Lactobacillus bulgaricus, Lactobacillus casei*, and *Streptococcus thermophilus*.

The enzymes may be any one or more selected from the group consisting of: amylase, papain, cellulase, lactase, lipase, protease, and bromelain.

In accordance with a particularly preferred embodiment, the nutritional compositions may comprise all of the above-listed ingredients and is provided in a solid powdered form which may be added to a beverage of the user's choosing. It is believed that the combination of the adaptogens, superfoods, enzymes and probiotics provide a synergistic effect in the reduction of oxidative damage in the body. This synergistic effect is believed to result from the specific combination of adaptogens and the antioxidant capacity of the superfoods, which is significantly enhanced by the action of the enzymes and probiotics which make the special nutrients and antioxidants in the adaptogens and superfoods substantially more bioavailable.

In addition to the adaptogens, superfoods, enzymes and probiotics, the nutritional compositions may further comprise various plant products, algae, vitamins and minerals, and sources of protein and other nutrients so as to be suitable as a complete meal replacement.

Other objects, features and advantages of the present invention will become apparent to those skilled in the art from the following detailed description.

DETAILED DESCRIPTION OF THE EMBODIMENTS

A more complete appreciation of the disclosure and many of the attendant advantages will be readily obtained, as the same becomes better understood by reference to the following detailed description of the exemplary embodiments.

The nutritional compositions comprise at least one adaptogens. Adaptogens refer to agents which raises the body's nonspecific resistance to various physical, chemical or biological stressors. Adaptogens generally accomplish this by either regulating the activity of hyperfunctioning systems.

In the preferred embodiment, the nutritional compositions comprise at least one, preferably all, of the adaptogens listed in Table 1. The adaptogens may be provided in powdered form, and the amounts listed in Table 1 correspond to the weight per serving in powdered form. It is understood that the adaptogens listed in Table 1, and the amounts provided therein, are exemplary and may be substituted with other adaptogens which are both non-toxic to the subject and are capable of raising the body's nonspecific resistance to external stressors.

TABLE 1

| ADAPTOGENS | |
|---|---|
| Astragalus root | 100-300 mg |
| Cordyceps | 50-150 mg |
| Maca root | 500-1,500 mg |
| Schisandra berry | 25-75 mg |
| Ashwagandha root | 50-150 mg |
| Holy basil leaf | 25-75 mg |
| Reishi mushroom | 50-150 mg |
| Suma root | 25-75 mg |

In addition to the adaptogens, the nutritional compositions comprise at least one superfoods. Superfoods are understood to refer generally to foods which have nutritional significance due to their nutrient richness and high antioxidant capacity. Antioxidant capacity may be measured through a number of assays, such as oxygen radical absorbance capacity (ORAC), ferric ion reducing antioxidant power (FRAP), and trolox equivalence antioxidant capacity (TEAC) assays. The ORAC assay is considered by some to be a preferable method because of its biological relevance to the in vivo antioxidant efficacy. The Nutrient Data Laboratory (NDL) of the ARS\USDA has developed a database on the ORAC and total phenolic compounds (TP) of 275 selected foods (www.ars.usda.gov/SP2UserFiles/Place/12354500/Data/ORAC/ORAC07.pdf-).

In the preferred embodiment, the nutritional compositions comprise at least one, preferably all, of the superfoods listed in Table 2. The superfoods may be provided in powdered form, and the amounts listed in Table 2 correspond to the weight per serving in powdered form. It is understood that the superfoods listed in Table 2, and the amounts provided therein, are exemplary and may be substituted with other superfoods having high antioxidant capacity such as, for example, elderberry, cranberry, guarana, mango, noni, seabuckthorn, and grapes, and in varying amounts.

TABLE 2

| SUPERFOODS | |
|---|---|
| Acerola | 100-500 mg |
| Bioflavonoids | 25-150 mg |
| Acai berry | 50-350 mg |
| Lyceum barbarium | 50-500 mg |
| Blueberry | 50-500 mg |
| Gingo biloba leaf | 10-75 mg |
| Camu camu | 50-500 mg |
| Pomegranate | 50-500 mg |
| Rose hips | 10-100 mg |
| Bilberry | 50-500 mg |
| Maitake mushroom | 25-300 mg |

While individual superfoods may have high antioxidant capacity, its effectiveness in vivo depends on its combination with other superfoods and also with other substances, such as enzymes and probiotics. Enzymes and probiotics increase the bioavailability of antioxidants contained in the superfoods and thus increase the antioxidant efficacy in the body in the most usable form.

Digestive enzymes, particularly those from plant sources such as pineapples and papayas, help the body break down food into individual components, making them easier to absorb. Because cooking typically destroys many of the food's digestive enzymes, prepared foods typically do not have sufficient amounts of these digestive enzymes. Thus, the enzymes aid the body in digesting foods having high antioxidant In the preferred embodiment, the nutritional compositions comprise at least one, preferably all, of the enzymes listed in Table 3. The amounts listed in Table 3 correspond to the weight per serving in powdered form. It is understood that the enzymes listed in Table 3, and the amounts provided therein, are exemplary and may be substituted with other digestive enzymes which do not interfere with the antioxidant capacity of the superfoods. The digestive enzymes in Table 3 are believed to increase the bioavailability of the antioxidants in the body for digestion and absorption in the relative amounts provided.

TABLE 3

| ENZYMES | |
|---|---|
| Amylase | 20-30 mg |
| Lipase | 15-25 mg |
| Cellulase | 15-25 mg |
| Bromelain | 0.1 mg |
| Protease | 15-25 mg |
| Lactase | 15-25 mg |
| Papain | 20-35 mg |

Probiotics refer generally to bacterial cultures which are intended to assist the body's naturally occurring gut flora, an ecology of microbes, to reestablish themselves. Probiotics aid in digestion and help with the body's absorption of nutrients, including antioxidants. Thus, the inclusion of probiotics in the superfood/enzyme mixture results in an even greater absorption of the antioxidants in the body.

In a particularly preferred embodiment, the nutritional compositions comprise at least one, and preferably all, of the probiotics listed in Table 4. The amounts listed in Table 4 correspond to the weight per serving for each of the probiotics in powdered form, and it is understood that the probiotics listed in Table 4, and the amounts provided therein, are exemplary and may be substituted with other probiotics which are known to benefit the body's gut flora and enhance in the digestion and absorption of nutrients.

TABLE 4

| PROBIOTICS | |
|---|---|
| Lactobacillus acidophilus | 20-30 mg |
| Lactobacillus bulgaricus | 20-30 mg |
| Streptococcus thermophilus | 20-30 mg |
| Lactobacillus acidophilus DDS-1 | 20-30 mg |
| Lactobacillus casei | 20-30 mg |
| Bifidobacterium longum | 20-30 mg |

It may be desirable to provide additional ingredients in the nutritional compositions, particularly if the nutritional compositions will be consumed as meal replacements. The additional ingredients may be selected to provide other complementary health benefits, such as weight control, immune support, as well as provide the nourishment that is required of a balanced meal. Suitable additional ingredients include plant products and algae. These substances provide a host of essential vitamins, nutrients, amino acids and protein.

Plant products are a source of numerous phytonutrients and phytochemicals which are believed to have numerous beneficial health properties, i.e., anti-cancer, anti-inflammatory, anti-viral, and anti-bacterial. There is evidence that phytochemicals in fruits and vegetables reduce the risk of cancer, possibly due to dietary fibers, polyphenol antioxidants and anti-inflammatory effects. Clinical investigations continue to assess many different phytochemicals with medicinal properties.

By including plant products, the nutritional composition not only provides the beneficial reduction in oxidative damage, it also provides needed nutrients and may thus be consumed as a meal replacement. The whole-food ingredients deliver the essential amino acids, vitamins and minerals that the body needs.

In a particularly preferred embodiment, the nutritional compositions additionally comprise at least one, and preferably all, of the plant products listed in Table 5. The amounts listed in Table 5 correspond to the weight per serving for each of the plant products in powdered form, and it is understood that the plant products listed in Table 5, and the amounts provided therein, are exemplary and may be substituted with other plant products which provide beneficial phytochemicals and nutrients that the body needs for the nutritional composition to be an effective meal replacement.

TABLE 5

| PLANT PRODUCTS | |
|---|---|
| Barley grass | 25-350 mg |
| Kamut grass | 25-350 mg |
| Hydrilla | 100-500 mg |
| Spinach | 50-500 mg |
| Whole flax seed meal | 250-1,000 mg |
| Chia seed | 100-1,000 mg |
| Grape seed extract | 25-150 mg |
| Pea fiber | 25-500 mg |
| Wheat grass | 25-450 mg |
| Oat grass | 25-450 mg |
| Sprouted amaranth | 10-100 mg |
| Sprouted quinoa | 25-450 mg |
| Green tea extract | 10-100 mg |
| Yacon root | 250-1,750 mg |
| Sacha inchi | 250-1,750 mg |
| Apple fiber | 50-600 mg |

Various algae species, such as blue-green algae, spirulina and chlorella, are believed to exert significant beneficial changes in cholesterol and blood pressure, including lowered total cholesterol, increased HDL cholesterol, lowered triglycerides, and lowered systolic and diastolic blood pressure. Additionally, these algae species have been linked to have anti-tumor and immune supporting properties. In addition to the health benefits, algae is a good source of protein, amino acids, and other nutrients.

Thus, in one preferred embodiment, the nutritional compositions may also further comprise at least one, preferably all, of the algae species listed in Table 6. The amounts listed in Table 6 correspond to the weight per serving for each of the algae species in powdered form and it is understood that the algae species listed in Table 6 and the amounts provided therein, are exemplary and may be substituted with other algae species which have similar beneficial effects as the ones listed therein.

TABLE 6

| ALGAE | |
|---|---|
| Blue green algae | 50-500 mg |
| Chlorella | 100-600 mg |
| Spirulina | 100-600 mg |

While many of the ingredients in the nutritional compositions are believed to provide whole food sources of the essential nutrients needed by the body, the nutritional compositions may be further supplemented with vitamins and minerals, proteins and methylsulfonylmethane (MSM). These additional supplements ensure that the nutritional compositions provide the needed nutrients so as to be suitable as meal replacements. In a preferred embodiment, the nutritional compositions additional comprise at least one, preferably all, of the vitamins and minerals listed in Table 7.

TABLE 7

| VITAMINS & MINERALS | |
|---|---|
| Vitamin A (as beta-carotene) | 5,000 IU |
| Vitamin C (as ascorbic acid) | 180 mg |
| Vitamin D (as cholecalciferol) | 200 IU |
| Vitamin E (as d-alpha tocopheryl succinate) | 15 IU |
| Vitamin K1 (as phytonadione) | 40 mcg |
| Vitamin B1 (as thiamin HCl) | 1.5 mg |
| Calcium (as dicalcium phosphate) | 500 mg |
| Phosphorus (as dicalcium phosphate) | 250 mg |
| Magnesium (as oxide) | 80 mg |
| Copper (as copper oxide) | 0.8 mg |
| Chromium (as chromium amino acid chelate) | 60 mcg |
| Vitamin B2 (as riboflavin) | 1.3 mg |
| Vitamin B3 (as niacin) | 5 mg |
| Vitamin B6 (as pyridoxine HCl) | 2 mg |
| Biotin | 90 mcg |
| Pantothenic acid (as d-calcium pantothenate) | 5 mg |
| Iron (as ferrous fumarate) | 5 mg |
| Iodine (as kelp) | 52 mcg |
| Zinc (as zinc oxide) | 6 mg |

TABLE 7-continued

| VITAMINS & MINERALS | | |
|---|---|---|
| Manganese (as manganese amino acid chelate) | 2 | mg |
| Molybdenum (as sodium molybdenate) | 30 | mcg |

In addition to the vitamins and minerals, suitable sources of protein may be included, such as whey protein (isolate). MSM may also be included in the nutritional compositions as a natural source of sulfur. MSM is currently believed to help in the treatment of a variety of ailments, including osteoarthritis.

The nutritional composition disclosed herein may be formulated in form of a solid, liquid or emulsion. Preferably, the nutritional composition is provided in solid form as a powder that may be added to a beverage or food of user's choice for ease of consumption. In a preferred embodiment, the nutritional composition is formulated in a solid powder form in the amounts described herein. Each serving (approximately 40 g) of the powder may be mixed with 8 ounces of cold water, milk, soy milk, rice milk, juice, or other beverage of the user's choosing.

The nutritional composition may be administered in any number of routes, depending on the form of the composition, including topical, oral, intravenous, transdermal, subcutaneous, enteral, inhalation, or parenteral. In a preferred embodiment, the nutritional composition is administered orally.

Various flavor ingredients may be added to enhance the flavor of the composition, such as fruit powders. In one embodiment, a fruity/berry flavor may be imparted on the nutritional composition by adding any one or a combination of banana, carrot, orange, pineapple, raspberry, and strawberry powders. In another embodiment, a chocolate flavor may be imparted by adding any one or a combination of chocolate, cocoa, and cinnamon powders. The relative concentration of the flavor ingredients in the formulation may be altered based on the desired taste. It is understood that additional ingredients may be added as flavor ingredients, so long as they do not interfere with the antioxidant effect of the composition.

EXAMPLE 1

In one embodiment, a nutritional supplement having the following ingredients is disclosed. With respect to ingredients which do not have the amounts listed below, reference is made to the amounts provided in Tables 1-7 above.

| Amount Per Serving | | | % Daily Value |
|---|---|---|---|
| Calories | 140 | | |
| Cholesterol | 10 | mg | 3% |
| Sodium | 95 | mg | 4% |
| Total Carbohydrate | 19 | g | 6% |
| Dietary Fiber | 3 | g | 13% |
| Sugars | 11 | g | |
| Protein | 15 | g | 30% |
| Vitamin A (as beta-carotene) | 5000 | IU | 100% |
| Vitamin C (as ascorbic acid) | 180 | mg | 300% |
| Vitamin D (as cholecalciferol) | 200 | IU | 50% |
| Vitamin E (as d-alpha tocopheryl succinate) | 15 | IU | 50% |
| Vitamin K1 (as phytonadione) | 40 | mcg | 50% |
| Vitamin B1 (as thiamin HCL) | 1.5 | mg | 100% |
| Vitamin B2 (as riboflavin) | 1.3 | mg | 77% |
| Vitamin B3 (as niacin) | 5 | mg | 25% |
| Vitamin B6 (as pyridoxine HCL) | 2 | mg | 100% |
| Folic acid | 200 | mcg | 50% |
| Vitamin B12 (as cyanobalamin) | 6 | mcg | 100% |
| Biotin | 90 | mcg | 30% |
| Pantothenic acid (as d-calcium pantothenate) | 5 | mg | 50% |
| Calcium (as dicalcium phosphate) | 500 | mg | 50% |
| Iron (as ferrous fumarate) | 4.5 | mg | 25% |
| Phosphorous (as dicalcium phosphate) | 250 | mg | 25% |
| Iodine (as kelp) | 52 | mcg | 35% |
| Magnesium (as oxide) | 60 | mg | 20% |
| Zinc (as zinc oxide) | 6 | mg | 40% |
| Copper (as copper oxide) | 0.8 | mg | 40% |
| Manganese (as manganese amino acid chelate) | 2 | mg | 100% |
| Chromium (as chromium amino acid chelate) | 60 | mcg | 50% |
| Molybdenum (as sodium molybdate) | 30 | mcg | 40% |
| Whey protein (isolate) | 15 | g | |
| SUPERFOOD BLEND: | 2075 | mg | |
| Acercia powder (fruit), Camu-Camu powder (fruit), Pomegranate powder (fruit), Bilberry powder (fruit), Blueberry powder (fruit), Lycium (Goji) powder (berry), Acai powder (berry), Cordyceps, Maitake powder, Reishi powder, Citrus bioflavonoids, Rose Hips powder (fruit), Schisandra powder (berry), Suma powder (root), Gingko powder (leaf). | | | |

| Amount Per Serving | | % Daily Value |
|---|---|---|
| FRUIT POWDER BLEND: | 1500 g | |
| Banana powder, Carrot powder, Orange powder, Pineapple powder, Raspberry powder, Strawberry powder | | |
| Maca powder (root) | 1000 mg | |
| Sacha inchi (*Plukenetia volubilis*) meal | 1000 mg | |
| Yacon (*smallanthus sonchitolius*) powder | 1000 mg | |
| Flax (seed) meal | 700 mg | |
| Chia (seed) meal | 500 mg | |
| Chlorella | 350 mg | |
| Spirulina | 350 mg | |
| Hydrilla | 300 mg | |
| Apple fiber powder | 250 mg | |
| Astragalus powder (root) | 200 mg | |
| Blue green algae | 200 mg | |
| Spinach powder | 200 mg | |
| MSM (methylsulfonylmethane) | 150 mg | |
| Pea fiber | 150 mg | |
| Quinoa (sprouted) | 150 mg | |
| PROBIOTIC BLEND: | 150 mg | |
| Bifodobacterium longum, Lactobacillus acidophilus, Lactobacillus acidophilus DDS-1, Lactobacillus bulgaricus, Lactobacillus casei, Streptococcus thermophilus. | | |
| ENZYME BLEND: | 130 mg | |
| Amylase, Papain, Cellulase, Lactase, Lipase, Protease, Bromelain. | | |
| Ashwagandha powder (root) | 100 mg | |
| Barley grass | 100 mg | |
| Kamut grass | 100 mg | |
| Oat grass | 100 mg | |
| Wheat grass | 100 mg | |
| Stevia | 75 mg | |
| Amaranth (sprouted) (*Amaranthus hypochondriacus*) | 50 mg | |
| Grape seed extract (seed, 95% proanthocyanins) | 50 mg | |
| Green tea decaffeinated extract (leaf, 50% polyphenols) | 50 mg | |
| Holy basil powder (leaf) | 50 mg | |

EXAMPLE 2

Twelve (12) subjects underwent antioxidant testing at the study onset and then after thirty (30) days of ingesting the nutritional composition described in Example 1. The total body antioxidant measurement was made using the Body Balance Antioxidant Test (Body Balance Laboratories). The test measured whole body free-radical activity by determining the rate of lipid peroxidation. A drop in lipid peroxidation is an indicator of a significant increase in blood antioxidant levels, reduction in free radicals, decreased cellular damage, and disease risk.

The rate of lipid peroxidation was measured for each of the twelve subjects at the study onset and after thirty (30) days of ingesting the nutritional composition at least once daily. The nutritional composition was provided to the subject in a powdered form and the subjects were instructed to add 40 g of the powder to 1 cup (8 fl. oz) cold water or beverage and mix. Each 40g serving of the powdered nutritional composition contained the ingredients and amounts listed in Tables 1-7 above. A comparison of the measurements of total body antioxidant at the onset and after 30 days showed an average decrease of 39%. One subject demonstrated a 90% decrease in lipid peroxidation.

Having thus described embodiments of the nutritional compositions for reducing oxidative damage, it should be apparent to those skilled in the art that certain advantages of the nutritional compositions have been achieved. It should also be appreciated that various modifications, adaptations, and alternative embodiments thereof may be made within the scope and spirit of the present invention.

What is claimed is:

1. An oral nutritional composition for reducing oxidative damage in humans said composition comprising a combination of:
   adaptogens comprising astragalus root, ashwagandha root, cordyceps, holy basil leaf, maca root, reishi mushroom, schisandra, and suma root;
   superfoods comprising acerola, camu-camu, pomegranate, bilberry, blueberry, Goji berries, Acai, maitake, citrus bioflavonoids, rose hips, and *Gingko biloba;*
   enzymes comprising amylase, papain, cellulase, lactase, lipase, protease, and bromelain; and
   probiotics comprising *Bifidobacterium longum, Lactobacillus acidophilus, Lactobacillus acidophilus* DDS-1, *Lactobacillus bulgaricus, Lactobacillus casei,* and *Streptococcus thermophilus.*

2. The nutritional composition of claim 1 further comprising plant products comprising wheat grass, barley grass, oat grass, hydrilla, kamut grass, spinach, sprouted amaranth, whole flax seed meal, sprouted quinoa, chia seed, green tea extract, grape seed extract, yacon root, sacha inchi, pea fiber, and apple fiber.

3. The nutritional composition of claim 1 further comprising algae comprising blue green algae, spirulina, and chlorella.

4. The nutritional composition of claim 1 further comprising vitamins comprising vitamin A, vitamin C, vitamin D, vitamin E, vitamin K1, vitamin B1, vitamin B2, vitamin B3, vitamin B6, folic acid, vitamin B12, biotin, and pantothenic acid.

5. The nutritional composition of claim 1 further comprising minerals comprising calcium, iron, phosphorus, iodine, magnesium, zinc, copper, manganese, chromium, and molybdenum.

6. The nutritional composition of claim 1 comprising adaptogens, superfoods, enzymes, and probiotics as provided below:

| ADAPTOGENS | | | |
|---|---|---|---|
| *Astragalus* root | 100-300 mg | *Ashwagandha* root | 50-150 mg |
| *Cordyceps* | 50-150 mg | Holy basil leaf | 25-75 mg |
| *Maca* root | 500-1,500 mg | *Reishi* mushroom | 50-150 mg |
| *Schisandra* berry | 25-75 mg | Suma root | 25-75 mg |
| SUPERFOODS | | | |
| *Acerola* | 200-400 mg | Camu camu | 150-350 mg |
| Bioflavonoids | 25-75 mg | *Pomegranate* | 150-350 mg |
| *Acai* berry | 100-200 mg | Rose hips | 25-75 mg |
| *Lycium barbarium* | 100-300 mg | Bilberry | 100-300 mg |
| Blueberry | 100-300 mg | *Maitake* mushroom | 50-150 mg |
| Gingo biloba leaf | 20-30 mg | | |
| ENZYMES | | | |
| Amylase | 20-30 mg | Protease | 15-25 mg |
| Lipase | 15-25 mg | Lactase | 15-25 mg |
| Cellulase | 15-25 mg | Papain | 20-30 mg |
| Bromelain | 0.1 mg | | |
| PROBIOTICS | | | |
| *Lactobacillus acidophilus* | 20-30 mg | *Lactobacillus acidophilus* DDS-1 | 20-30 mg |
| *Lactobacillus bulgaricus* | 20-30 mg | *Lactobacillus casei* | 20-30 mg |
| *Streptococcus thermophilus* | 20-30 mg | *Bifidobacterium longum* | 20-30 mg. |

7. The nutritional composition of claim 6 further comprising plant products as provided below:

| PLANT PRODUCTS | |
|---|---|
| Barley grass | 50-200 mg |
| Kamut grass | 50-200 mg |
| Hydrilla | 200-400 mg |
| Spinach | 100-300 mg |
| Whole flax seed meal | 500-900 mg |
| Chia seed | 250-750 mg |
| Grape seed extract | 25-75 mg |
| Pea fiber | 50-250 mg |
| Wheat grass | 50-200 mg |
| Oat grass | 50-200 mg |
| Sprouted amaranth | 25-75 mg |
| Sprouted quinoa | 50-250 mg |
| Green tea extract | 25-75 mg |
| Yacon root | 500-1,500 mg |
| Sacha inchi | 500-1,500 mg |
| Apple fiber | 100-400 mg. |

8. The nutritional composition of claim 6 further comprising algae as provided below:

| ALGAE | |
|---|---|
| Blue green algae | 100-300 mg |
| Chlorella | 250-450 mg |
| Spirulina | 250-450 mg. |

9. The nutritional composition of claim 6 further comprising vitamins and minerals as provided below:

| VITAMINS & MINERALS | |
|---|---|
| Vitamin A (as beta-carotene) | 5,000 IU |
| Vitamin C (as ascorbic acid) | 180 mg |
| Vitamin D (as | 200 IU |

| VITAMINS & MINERALS | |
|---|---|
| cholecalciferol) | |
| Vitamin E (as d-alpha tocopheryl succinate) | 15 IU |
| Vitamin K1 (as phytonadione) | 40 mcg |
| Vitamin B1 (as thiamin HCl) | 1.5 mg |
| Calcium (as dicalcium phosphate) | 500 mg |
| Phosphorus (as dicalcium phosphate) | 250 mg |
| Magnesium (as oxide) | 80 mg |
| Copper (as copper oxide) | 0.8 mg |
| Chromium (as chromium amino acid chelate) | 60 mcg |
| Vitamin B2 (as riboflavin) | 1.3 mg |
| Vitamin B3 (as riacin) | 5 mg |
| Vitamin B6 (as pyridoxine HCl) | 2 mg |
| Biotin | 90 mcg |
| Pantothenic acid (as d-calcium pantothenate) | 5 mg |
| Iron (as ferrous fumarate) | 5 mg |
| Iodine (as kelp) | 52 mcg |
| Zinc (as zinc oxide) | 6 mg |
| Manganese (as manganese amino acid chelate) | 2 mg |
| Molybdenum (as sodium molybdenate) | 30 mcg |
| vitamin B12 | 6 mcg. |

10. An oral nutritional composition in powdered form for reducing oxidative damage in humans said composition comprising a combination of:

adaptogens comprising astragalus, ashwagandha, cordyceps, maca root, reishi mushroom, and suma root;

superfoods comprising acerola, camu-camu, pomegranate, bilberry, blueberry, Goji, Acai, maitake, citrus bioflavonoids, and rose hips;

enzymes comprising amylase, papain, lactase, lipase, protease, and bromelain; and probiotics comprising *Bifidobacterium longum, Lactobacillus bulgaricus, Lactobacillus casei,* and *Streptococcus thermophilus.*

11. The nutritional composition of claim 10, wherein the adaptogens further comprise schisandra.

12. The nutritional composition of claim 10, wherein the enzymes further comprise cellulase.

13. The nutritional composition of claim 10, wherein the adaptogens further comprise holy basil leaf.

14. The nutritional composition of claim 10, wherein the superfoods further comprise *Gingo biloba.*

15. The nutritional composition of claim 10, wherein the probiotics further comprise *Lactobacillus acidophilus.*

* * * * *